(12) United States Patent
Hurtado

(10) Patent No.: US 8,133,201 B1
(45) Date of Patent: Mar. 13, 2012

(54) TEMPLATE FOR INJECTION PLACEMENT

(76) Inventor: Paola Hurtado, Miami, FL (US)

( * ) Notice: Subject to any disclaimer, the term of this patent is extended or adjusted under 35 U.S.C. 154(b) by 46 days.

(21) Appl. No.: 12/387,557

(22) Filed: Nov. 6, 2009

(51) Int. Cl.
  *A61M 5/00* (2006.01)
(52) U.S. Cl. ...................................................... 604/116
(58) Field of Classification Search .................. 604/116; 128/849–856; 33/23.11, 562–566; 132/319
  See application file for complete search history.

(56) References Cited

U.S. PATENT DOCUMENTS 4,228,796 A * 10/1980 Gardiner ........................ 604/116
4,856,509 A * 8/1989 Lemelson ................ 128/206.19
* cited by examiner

*Primary Examiner* — Laura Bouchelle
(74) *Attorney, Agent, or Firm* — Albert Bordas, P.A.

(57) ABSTRACT

A template for identifying a specific location for insertion of a hypodermic injection device to inject insulin at specific areas of an abdomen. It comprises a flexible sheet having at least top and bottom edges and first and second lateral edges. The exterior face has a hole and at least one legend. The at least one legend comprises a calendar reference and first and second marking holes. The exterior face further comprises at least one offset hole at a predetermined distance from the hole. The calendar reference defines dates or days of a week. The calendar reference is positioned in between the first and second marking holes. The first and second marking holes serve as identifying means for identifying a specific location for insertion of a hypodermic injection device to inject insulin at specific areas of an abdomen in between the first and second marking holes.

1 Claim, 3 Drawing Sheets

TEMPLATE FOR INJECTION PLACEMENT

BACKGROUND OF THE INVENTION

1. Field of the Invention

The present invention relates to medical instruments, and more particularly, to a template used to facilitate injecting of insulin at specific areas of the abdomen.

2. Description of the Related Art

Diabetes is a disease or disorder, which is unfortunately shared by many people both young and old. The condition is characterized by an inadequate secretion or utilization of insulin, which results in excessive amounts of sugar in the blood. In many cases, observing a strict diet can control the condition. In other more serious cases, it can only be controlled by regular injections of insulin. For those serious cases, an insulin injection must be applied daily, or in some cases, twice a day. Most people who must take insulin injections are taught to administer the injections themselves. In recent years, even relatively young children have been taught to administer their own insulin injections.

A recommended injection site for insulin is a fatty layer of the user's abdomen. Arms, legs and buttocks are not usually recommended as the absorption of insulin varies and may work too quickly if exercise is undertaken soon after injection. It is also recommended by doctors that patients change the spot of injection each time to avoid fatty lumps forming under the skin and other adverse conditions, which take four to six weeks for the tissue to repair. Therefore, users of insulin are taught to inject themselves in a different spot on the same area each time. Unfortunately, many people may forget where they gave themselves the last injection and may tend to continually give themselves injections in the same location.

Applicant is not aware of any templates to facilitate injecting of insulin at specific areas of the abdomen having the novel features of the present invention.

SUMMARY OF THE INVENTION

The instant invention is a template for identifying a specific location for insertion of a hypodermic injection device to inject insulin at specific areas of an abdomen. It comprises a flexible sheet having at least top and bottom edges and first and second lateral edges. The flexible sheet also has an exterior face defining first and second template areas. The exterior face has a hole and at least one legend. The at least one legend comprises a calendar reference, each having respective first and second marking holes.

The hole is a centrally located on the exterior face. The instant invention further comprises at least one offset hole at a predetermined distance from the hole. The at least one offset hole is on a same axis as the hole. The calendar reference defines dates or days of a week. Each calendar reference is positioned in between its respective first and second marking holes. The first and second marking holes serve as identifying means for identifying a specific location for insertion of the hypodermic injection device to inject insulin at a specific area of an abdomen in between the respective first and second marking holes. The flexible sheet further comprises first and second through holes, and the instant invention further comprises a strap member. The strap member comprises a strap having at least one lock tab at a distal end. The strap extends from the first to the second through hole. The strap can be elastic.

It is therefore one of the main objects of the present invention to provide a template for identifying a specific location for insertion of a hypodermic injection device to inject insulin at specific areas of an abdomen.

It is another object of this invention to provide a template for identifying a specific location for insertion of a hypodermic injection device to inject insulin at specific areas of an abdomen that allows a fixed point, the naval of the user, as point of reference for the template.

It is another object of this invention to provide a template for identifying a specific location for insertion of a hypodermic injection device to inject insulin at specific areas of an abdomen that provides for injection rotation.

It is another object of this invention to provide a template for identifying a specific location for insertion of a hypodermic injection device to inject insulin at specific areas of an abdomen that allows for changing of the spot of injection each time to avoid fatty lumps forming under the skin and others adverse conditions, which take four to six weeks for the tissue to repair.

It is yet another object of this invention to provide such a template that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
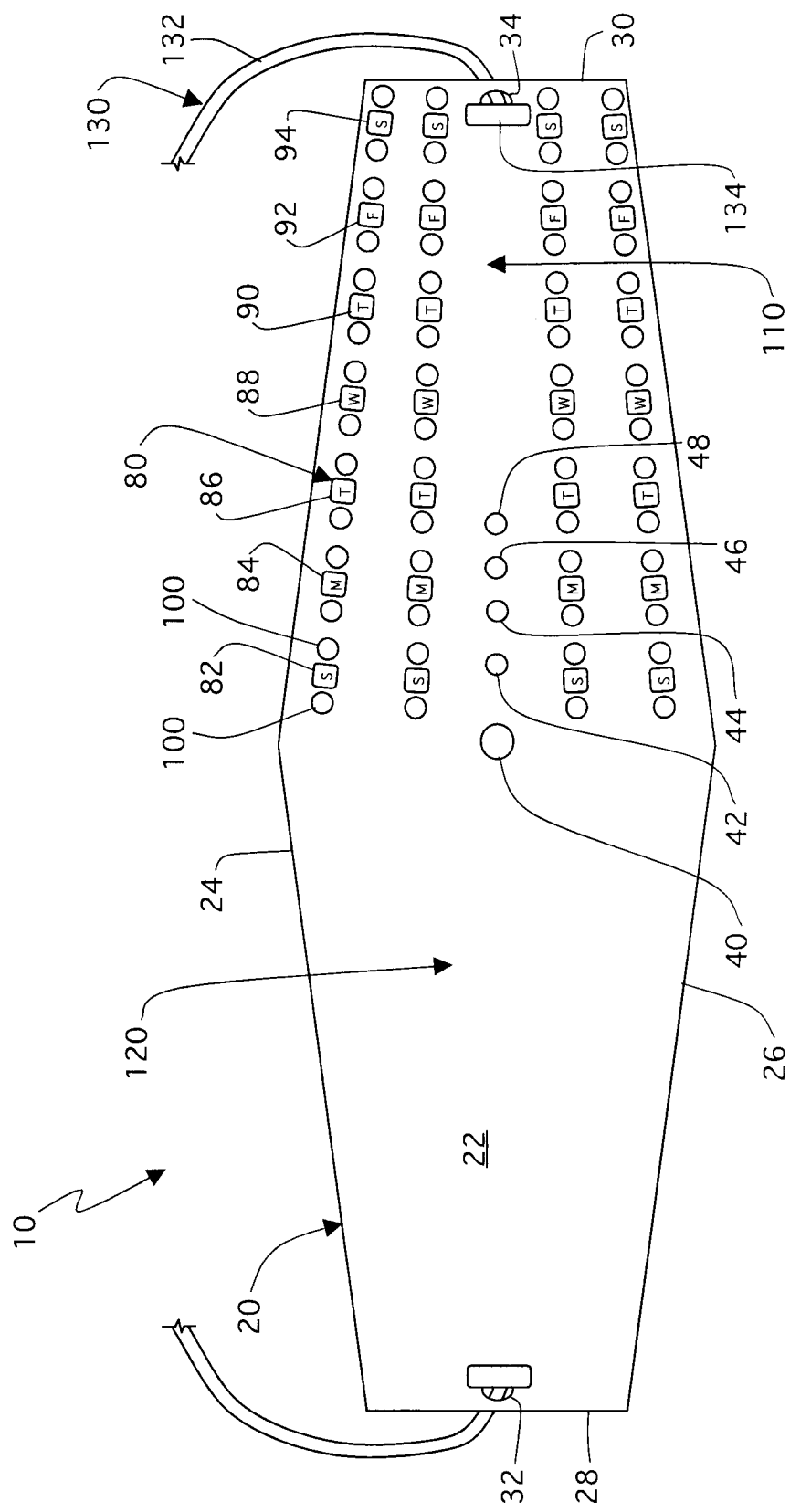
FIG. 1 is a front elevational view of a preferred embodiment of the instant invention.

Referring now to the drawings, the present invention is generally referred to with numeral 10. It can be observed that it basically includes flexible sheet 20 and strap member 130.

Figure 2:
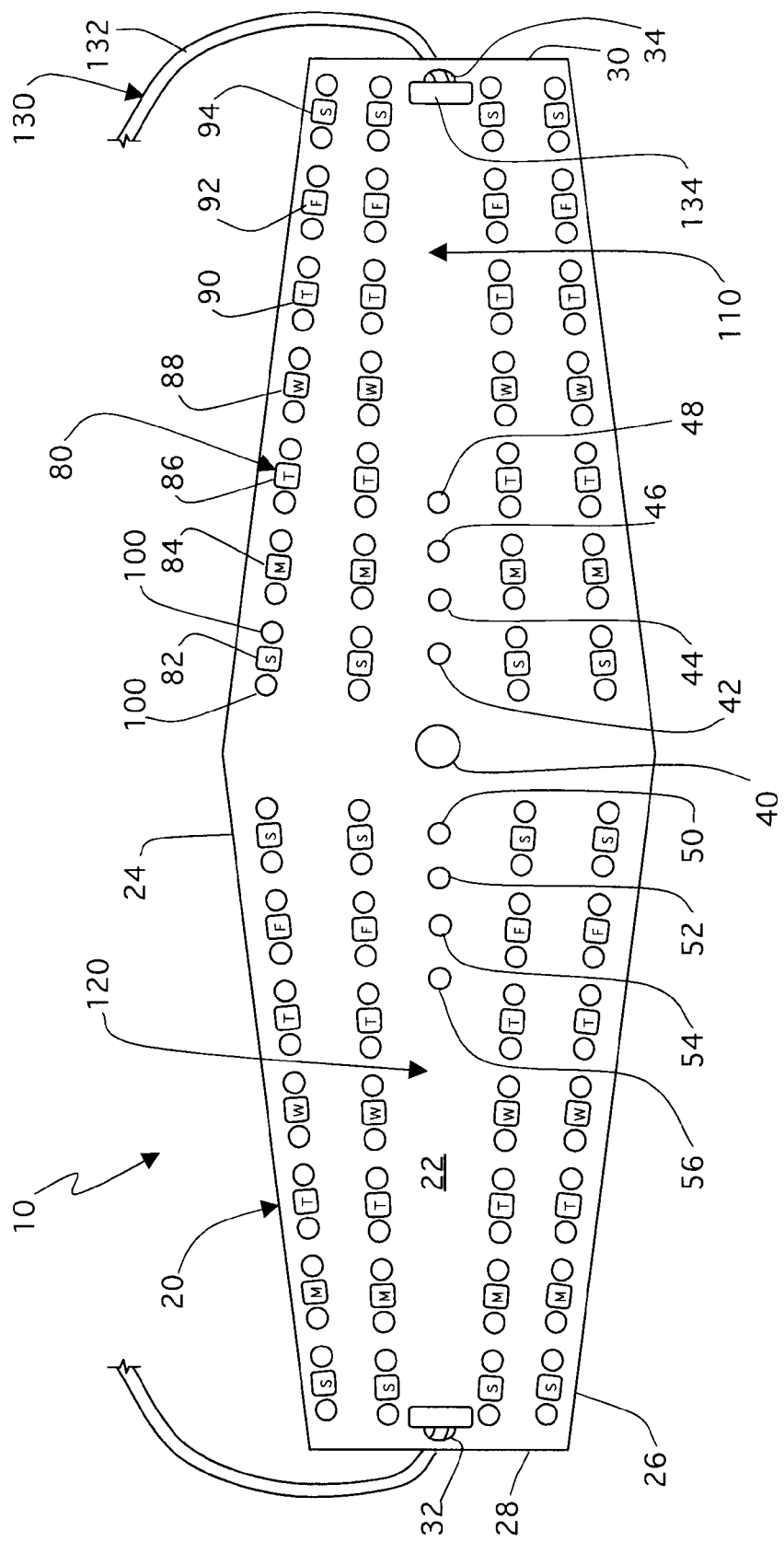
FIG. 2 is a front elevational view of an alternate embodiment of the instant invention.

As seen in FIGS. 1 and 2, instant invention 10 is a template for identifying a specific location for insertion of a hypodermic injection device to inject insulin at specific areas of an abdomen.

Instant invention 10 comprises flexible sheet 20 having top edge 24, bottom edge 26, and lateral edges 28 and 30. Flexible sheet 20 also has exterior face 22 that defines template areas 110 and 120. Exterior face 22 has hole 40 and at least one legend 80. In the preferred embodiment, hole 40 is centrally located on exterior face 22. Exterior face 22 also comprises at least one offset hole. In a preferred embodiment, such offset holes include 42; 44; 46; and 48, each at a predetermined distance from hole 40 at template area 110. And offset holes 50; 52; 54; and 56, are each also at a predetermined distance from hole 40 at template area 120. Offset holes 42; 44; 46; 48; 50; 52; 54; and 56 are on a same axis as hole 40. Flexible sheet 20 further comprises through holes 32 and 34.

Instant invention 10 also comprises strap member 130. Strap member 130 comprises strap 132 having at least one lock tab 134 at a distal end. Strap 132 extends from through hole 32 to 34. In the preferred embodiment strap 132 is elastic.

Each legend 80 may comprise calendar references 82; 84; 86; 88; 90; 92; and 94 that correspond to days of a week. Specifically, calendar reference 82 defines Sunday of a calendar week; calendar reference 84 defines Monday of the calendar week; calendar reference 86 defines Tuesday of the calendar week; calendar reference 88 defines Wednesday of the calendar week; calendar reference 90 defines Thursday of the calendar week; calendar reference 92 defines Friday of the calendar week; and calendar reference 94 defines Saturday of the calendar week. The above calendar reference may define days of a week as illustrated or calendar dates of a month such as 1; 2; 3; and so forth through 28; 29; 30; or 31.

Each calendar reference 82; 84; 86; 88; 90; 92; and 94 comprises its respective marking holes 100. Each calendar reference 82; 84; 86; 88; 90; 92; and 94 is positioned in between its respective marking holes 100. Marking holes 100 serve as identifying means for identifying a specific location for insertion of the hypodermic injection device to inject the insulin at specific areas of the abdomen in between the respective marking holes 100 of the corresponding calendar reference.

Figure 3:
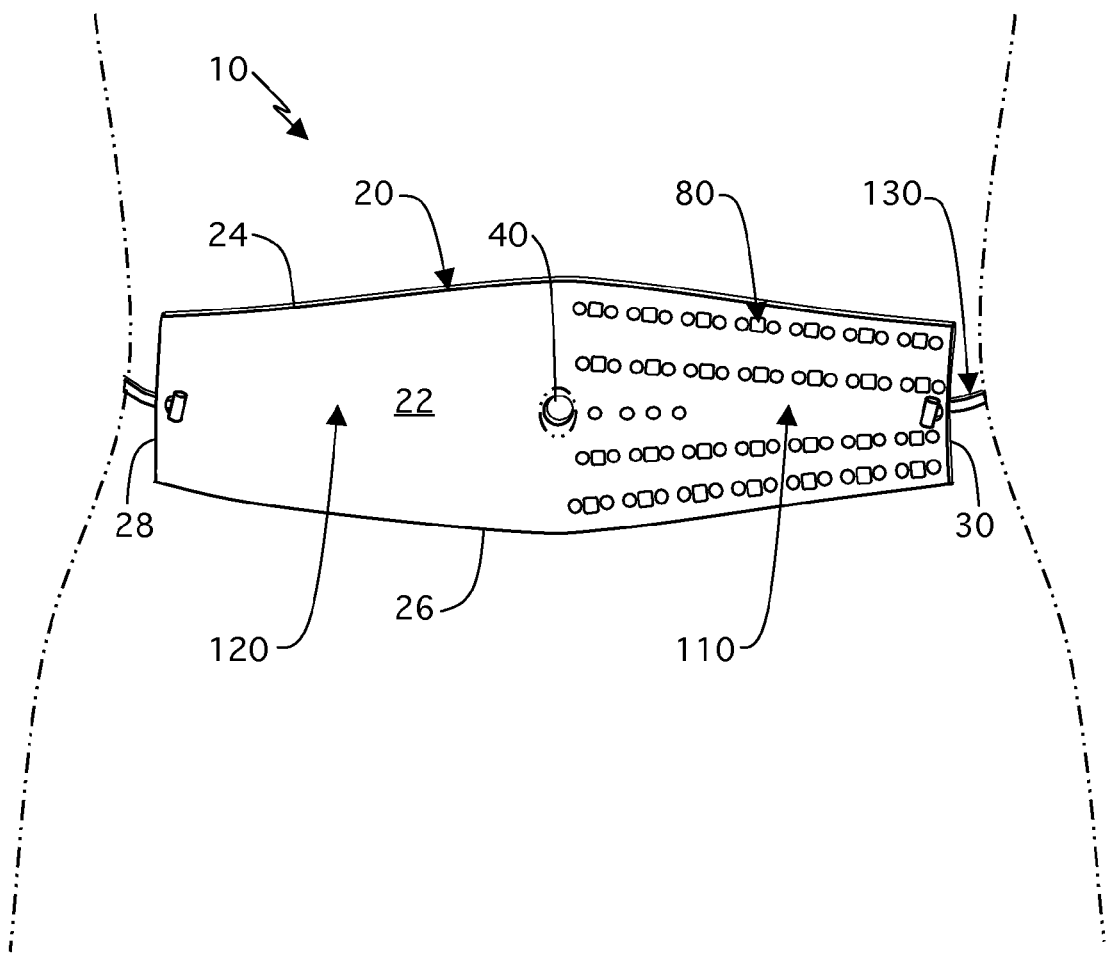
FIG. 3 is an isometric view of the instant invention as worn by a user.

As seen in FIG. 3, assuming use of instant invention 10 for a first time, described is Day 1:

A user places instant invention 10 onto his/her abdomen so that hole 40 aligns with/is positioned over his/her naval. The user may secure instant invention 10 around his/her waist with strap member 130. The user then identifies a specific legend 80 to use and identifies the corresponding day of the week according to the calendar. As mentioned above, marking holes 100 serve as identifying means for identifying a specific location for insertion of the hypodermic injection device to inject the insulin at specific areas of the abdomen in between the respective marking holes 100 of the corresponding calendar reference. As an example, the user may identify calendar reference 82 if it is a Sunday. The user then takes a vanishing non-toxic marker and marks through the respective marking holes 100 of the corresponding calendar reference 82 to mark his/her abdomen area. The user removes instant invention 10 therefrom. The user having identified the specific location for insertion of the hypodermic injection device to inject the insulin proceeds to inject the insulin in between the marks made through the respective marking holes 100.

Day 2: the user places instant invention 10 onto his/her abdomen so that hole 40 aligns with/is positioned over his/her naval. The user may secure instant invention 10 around his/her waist with strap member 130. The user then identifies the specific legend 80 to use and identifies the corresponding day of the week according to the calendar. The user identifies calendar reference 84 for Monday. The user then takes the vanishing non-toxic marker and marks through the respective marking holes 100 of the corresponding calendar reference 84 to mark his/her abdomen area. The user removes instant invention 10 therefrom. The user having identified the specific location for insertion of the hypodermic injection device to inject the insulin proceeds to inject the insulin in between the marks made through the respective marking holes 100.

Day 3: the user places instant invention 10 onto his/her abdomen so that hole 40 aligns with/is positioned over his/her naval. The user may secure instant invention 10 around his/her waist with strap member 130. The user then identifies the specific legend 80 to use and identifies the corresponding day of the week according to the calendar. The user identifies calendar reference 86 for Tuesday. The user then takes the vanishing non-toxic marker and marks through the respective marking holes 100 of the corresponding calendar reference 86 to mark his/her abdomen area. The user removes instant invention 10 therefrom. The user having identified the specific location for insertion of the hypodermic injection device to inject the insulin proceeds to inject the insulin in between the marks made through the respective marking holes 100.

Once the user completes a week of legend 80, he/she may select a following/another legend defined on exterior face 22 to repeat the same steps described above, but at a different location of the user's abdomen. It is noted that legends may be defined on just one side of exterior face 22, such as on template area 110 seen in FIG. 1, or on both sides of exterior face 22, such as on template areas 110 and 120. Further optimization of instant invention 10 may include the user's desire to shift instant invention 10, whereby the user places instant invention 10 onto his/her abdomen so that any one of offset holes 42; 44; 46; 48; 50; 52; 54; or 56 align with/is positioned over his/her naval instead. Thus, achieving a different specific location for insertion of the hypodermic injection device to inject the insulin in between the marks made through the respective marking holes 100.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A template for identifying a specific location for insertion of a hypodermic injection device to inject insulin at an abdomen, comprising a flexible sheet having top and bottom edges and first and second lateral edges, said flexible sheet having an exterior face defining first and second template areas, said exterior face having a hole and at least one legend, each said at least one legend having calendar references, each of said calendar references comprises respective first and second marking holes, said hole is centrally located on said exterior face and aligned and positioned over a naval of a user, said flexible sheet has at least one offset hole at a predetermined distance from said hole, said at least one offset hole is on a same axis as said hole, each said calendar references defines a date or day of a week, said flexible sheet further comprises first and second through holes, each said calendar references is positioned in between its respective said first and second marking holes that are separate from any other marking holes, and said first and second marking holes are not used for any other calendar reference, said first and second marking holes serve as identifying means for identifying a specific location for insertion of a hypodermic injection device to inject insulin at said abdomen in between respective said first and second marking holes, said flexible sheet further comprises a strap member, said strap member comprises a strap having at least one lock tab at a distal end, said strap extends from said first to said second through hole, and said strap is elastic.

* * * * *